United States Patent
Finmans et al.

(10) Patent No.: US 7,943,798 B2
(45) Date of Patent: May 17, 2011

(54) PROCESS FOR PREPARING METAL SALTS OF UNSATURATED, SHORT-CHAIN CARBOXYLIC ACIDS AND USE THEREOF

(75) Inventors: Peter Finmans, Duisburg (DE); Detlef Hoell, Moers (DE); Eveline Nickel, Rheinberg (DE); Elmar Gramse, Moers (DE)

(73) Assignee: Sasol Solvents Germany GmbH, Hamburg (DE)

( * ) Notice: Subject to any disclaimer, the term of this patent is extended or adjusted under 35 U.S.C. 154(b) by 953 days.

(21) Appl. No.: 10/563,237

(22) PCT Filed: Jul. 2, 2004

(86) PCT No.: PCT/DE2004/001414
§ 371 (c)(1),
(2), (4) Date: May 8, 2007

(87) PCT Pub. No.: WO2005/005364
PCT Pub. Date: Jan. 20, 2005

(65) Prior Publication Data
US 2007/0287747 A1 Dec. 13, 2007

(30) Foreign Application Priority Data
Jul. 3, 2003 (DE) .................. 103 30 217

(51) Int. Cl.
*C07C 57/02* (2006.01)
(52) U.S. Cl. ........................................ 562/598
(58) Field of Classification Search .................. None
See application file for complete search history.

(56) References Cited

U.S. PATENT DOCUMENTS

| | | | |
|---|---|---|---|
| 2,844,551 A * | 7/1958 | Orthner et al. ................ 528/271 |
| 2,940,957 A | 6/1960 | Herman et al. | |
| 3,337,391 A | 8/1967 | Clayton et al. | |
| 3,923,716 A | 12/1975 | Powanda et al. | |
| 3,957,598 A | 5/1976 | Merkl | |
| 5,952,151 A | 9/1999 | Sondergeld | |
| 5,998,646 A * | 12/1999 | Riondel et al. .................. 556/55 |

FOREIGN PATENT DOCUMENTS

| | | |
|---|---|---|
| BE | 763157 | 7/1971 |
| FR | 1205366 * | 2/1960 |
| JP | 48091012 | 11/1973 |
| JP | 63247037 | 10/1988 |
| JP | 04008298 | 1/1992 |
| RU | SU614089 | 7/1978 |

* cited by examiner

Primary Examiner — Karl J Puttlitz

(57) ABSTRACT

The present invention relates to the use of metal compounds of unsaturated, short-chain carboxylic acids. The invention also relates to a method for preparing metal compounds of unsaturated, short-chain carboxylic acids by reaction of said acids with a metal alcoholate.

13 Claims, No Drawings

PROCESS FOR PREPARING METAL SALTS OF UNSATURATED, SHORT-CHAIN CARBOXYLIC ACIDS AND USE THEREOF

BACKGROUND OF THE INVENTION

1. Field of the Invention

It is an object of this invention to provide a method for preparing metal salts of unsaturated, short-chain carboxylic acids by reaction of unsaturated carboxylic acids with metal alcoholates. Furthermore, the uses of metal salts of unsaturated, short-chain carboxylic acids are also an object of this invention.

2. Description of the Prior Art

The homologues of mono-unsaturated carboxylic acids have the general empirical formula $C_nH_{2n-1}$—COOH. These colourless liquids, when short-chained, are water-miscible at any ratio and tend to polymerize to form a glassy mass. The metal salts of acrylic acid, too, are colourless. They can be produced in solution or as a powder.

Methods for preparing aluminium salts of acrylic acid are known per se. For example, JP 48091012 describes the preparation of aluminium acrylate and the basic (or complex) salts thereof by reaction of $Al(OH)_3$ gel or basic aluminium sulfate obtained as an insoluble salt from an aqueous solution of $Al_2(SO_4)_3$ by eliminating all or part of the $SO_4^{2-}$, with pure acrylic acid or a mixture of acrylic acid and an organic or inorganic acid. However, the formation of salts, which contaminate the product or need to be separated by a laborious separation step, is a disadvantage of said method.

The preparation of carboxylic acid metal salts has also been disclosed in U.S. Pat. No. 3,957,598. As reported, a metal salt of a carboxylic acid is formed by contacting a carboxylic acid with an activated metal. The activated metal is formed by combining a first metal with a second metal, which has an affinity for hydrogen in the presence of a proton source. Activated aluminium from a highly pure aluminium rod is caused to react with an alloy of gallium and indium in the presence of hydrochloric acid. The addition of excess water in the presence of the carboxylic acid and activated metal forms a polymeric metal salt from a water-soluble carboxylic acid.

It is a disadvantage of said method that an alloy of aluminium metals is required, which comprises components part of which are highly precarious in environmental aspects and can only be recovered by very expensive separation techniques.

U.S. Pat. No. 3,923,716 describes the preparation of aluminium acrylate in two steps. First, acrylic acid is added to aqueous sodium hydroxide to form sodium acrylate, which then is caused to react with aluminium trichloride to form (mono-, di-, tri-) aluminium acrylate and sodium chloride. Since the aluminium acrylate is poorly soluble, it can easily be separated from the dissolved sodium chloride and the aqueous reaction mixture. The disadvantage of said method, however, is the large quantity of hydrochloric acid which is dissolved in water and partially contaminated with product and needs to be disposed of.

The preparation of the corresponding salts of titanium is known from U.S. Pat. No. 5,998,646. However, the continuous feeding of oxygen for the reaction and a certain degree of $O_2$ saturation has not been disclosed therein. On the contrary, the reaction is carried out at reduced pressure, with exclusion of air, and at elevated temperature, so that the absence of oxygen and a solvent atmosphere can be expected.

SUMMARY OF THE INVENTION

It is an object of this invention to eliminate the shortcomings described hereinabove and, in particular, to provide a method for producing solely unobjectionable by-products which can be separated easily and completely and which is useful for producing very pure carboxylic acid metal salts of various metal ions, preferably without formation of undesired polymeric compounds and without the need of additional, laborious purifying steps.

According to the present invention, the problem has been resolved by a method for preparing metal salts of unsaturated, short-chain carboxylic acids by reaction
of metal-alcoholate compounds
with carboxylic acids of the general formula $$C_nH_{2n-1}C(=O)OH,$$

wherein the double bond is in 2- or 3-position and
n represents 2, 3, 4, 5, or 6 and/or maleic acid (less desirable), in the presence of oxygen, which is continuously fed so that its concentration in the reaction solution is at least 50%, i.e., the reaction solution is 50% oxygen-saturated and
the metal salts have at least one group of the formula $$C_nH_{2n-1}C(=O)O\text{—, and/or —}OC(=O)CH=CHC(=O)O\text{—(H)}$$

and the following metals or mixtures thereof.
Al, Si, Sn, La, Zr, Cu and/or Zn.

Especially the metal salts of unsaturated, short-chain carboxylic acids have the general formula
$$M(OOCC_nH_{2n-1})_a(R^1)_b$$
and can be obtained by reaction of a linear or branched, unsaturated carboxylic acid of the formula $$C_nH_{2n-1}\text{—COOH,}$$

wherein n represents 2, 3, 4, 5, or 6 with the double bond in 2- or 3-position, preferably in 2-position, with a metal compound of the general formula $$M(R^1)_c$$

and, optionally, among others $$H(R^1),$$

wherein
a is at least 1,
b is 0, 1, 2 or 3 and
(a+b) and c are independently of one another an integer of 2 to 4,
M is Al, Si, Sn, La, Zr, Cu, or Zn, particularly Al or Zr, $R^1$ represents an alcoholate group having a $C_1$- to $C_6$ hydrocarbons residue, wherein $R^1$ is a saturated, linear or branched alcoholate group, which can be obtained from an alcohol having at least one —OH group, wherein the —OH groups are preferably primary and/or secondary —OH groups, or

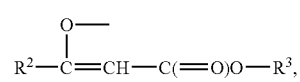

wherein $R^2$ or $R^3$ represent —$CH_3$, —$C_2H_5$, —$C_3H_7$ or —$C_4H_9$
and n, $R^1$, $R^2$, and $R^3$ may be different for each a, b, and c and at least one $R^1$ in $M(R^1)_c$ represents an alcoholate group having a $C_1$- to $C_6$ hydrocarbons residue, in the presence of oxygen ($O_2$), which is continuously fed so that its concentration in the reaction is at least 50% as set forth above.

The preferred embodiments of the subject invention are set out in the additional independent claim 2, the subordinate claims, or are described hereinbelow.

DESCRIPTION OF PREFERRED EMBODIMENTS

According to the present invention, the reaction is carried out in the presence of oxygen so that the reaction solution contains at least 50% oxygen, preferably at least 90%, for example by feeding a gas mixture containing 5 to 30 vol % oxygen, preferably 15 to 25 vol %. The oxygen may also be present as a mixture with air, particularly if the mixture is dried. The oxygen inhibits the tendency of the product to polymerize during the manufacturing process.

According to the present invention, the process is carried out at temperatures from 0° C. to 150° C., preferably 20° C. to 100° C., most preferably at least for a short time at greater 40° C., and preferably at a pressure from 2 $bar_{abs}$ to 0.01 $bar_{abs}$.

With the exception of the aforementioned reactants which can be used in excess, no additional solvent or diluent is required in the process. If solvents are used, hydrocarbons, esters, particularly esters of $C_1$- to $C_{18}$ monocarboxylic acids with $C_1$- to $C_8$ alcohols and ether alcohols including polyols, ethers, glycols and/or glycol mono-/di-ethers are suitable.

According to the present invention, particularly preferable unsaturated carboxylic acids are acrylic acid and methacrylic acid or carboxylic acids of the formula R—CH=CH—$CH_2$—COOH.

The reacted metal compounds of the invention are metal alcoholates. The bound metal ion is an ion of the metals magnesium, calcium, aluminium, silicon, tin, lanthane, titanium, zirconium, copper, and zinc, preferably aluminium, zirconium, and titanium, particularly aluminium. Examples of metal alcoholates according to the present invention include aluminium tri-sec-butanolate, aluminium tri-isopropylate, zirconium tetrabutylate, titanium tetrabutylate, magnesium dibutylate. Particularly preferable metal alcoholates are alcoholates of alcohols having 3 to 4 hydrocarbon atoms, such as isopropanol, n-butanol, and sec-butanol, particularly isopropanol and sec-butanol. The alcohol group can optionally be prepared as well from a polyol.

The principal advantage of the process of the invention is the very simple preparation of a high-purity product, which may be obtained straight or dissolved in the aforementioned solvents. This novel process makes carboxylic acid salts of metals accessible, which can be made available in the form of alcoholates.

In comparison with conventional processes, the process of the invention offers among others the following improvements:
  simple synthesis route
  low tendency to polymerization
  higher purity with respect to the foreign ion, preferably less than 100 ppm of chloride and sulfate,
  applicable to metals which are available as alcoholates
  a high-purity product is obtained either as a solid or in solution.

The main uses of the metal compounds of unsaturated carboxylic acids of the invention, particularly of the aluminium mono- to tri-(meth)acrylate are the production of rubber, synthetic resins, flame retardants, coatings and additives therefor. These coatings may be applied to glass, ceramics, organic polymers, metals, papers, and cardboard.

Further uses of metal (meth)acrylates are:
  Corrosion control of metals, coating or production of fiberglass, sand moulds, paper, plastics etc., (direct current) wire sheathing, additives for building materials and UV-cured cements, light-sensitive imaging agents, photographic paper coatings, polishes, stabilizers for polymers, removal of waterborne pigmented paints, rheology-improving and antifungi additive and siccative for the production of lacquers, paints, and printing inks, and in medicine as a basis for gel plasters and dental cements.

Metal salts of unsaturated, short-chain carboxylic acids can be used in various protective coatings, e.g of. resins, such as alkyd-, epoxide- or acryl-containing polymers, which are useful for sealing worktops made of marble or natural stone, parquet or fiberboard. The resin makes the work surface very resistant to aggressive and/or corrosive chemicals and to mechanical and thermal stress. As to the field of hydraulic steelwork, offshore operations, and shipbuilding, epoxy resins are combined with bitumen or asphalt to make epoxy resin/tar coatings. Polyurethane coatings are required for making furniture, automobiles, and airplanes. Yet another field of applications comprises coatings for concrete surfaces, marble statues and similar stone sculptures. Phenolic resins are highly resistant to corrosion so that they are frequently employed for packaging foodstuffs, e.g of. canning. Modified phenolic resins are used for antifouling paints in maritime applications and as a basis for anticorrosive paints for sea- and land crafts.

The addition of metal salts of unsaturated, short-chain carboxylic acids to said resins improves for example the hardness while increasing at the same time the resistance to mechanical, thermal and chemical influences.

Further coatings in which metal salts of unsaturated, short-chain carboxylic acids may be employed according to the present invention are solvent- and/or water-containing lacquers, e.g of. alkyd-, PU-, NC-, epoxy-, and acryl resin lacquers, which are employed for sealing materials, such as metals, plastics, papers or cardboard, and wood in order to protect them from decomposition or aggressive influences, e.g of. antirust paint on an outdoor metal staircase railing or for ships. In the same way UV-protective paints for garden furniture, wood protective lacquers, or impregnating lacquers for paper or cardboard. Acryl resin lacquers are appreciated for lacquering plastics (phono/TV cases, toys, interior fittings for automobiles) because of their rapid drying and also as chemically crosslinking lacquers for high-grade, nonyellowing, weather-resistant coatings (2K lacquers, exterior-wall paints, stoving enamels). Air-drying alkyd-resin lacquers are basically used as architectural paints, but are also common as marine paints, machinery paints, and for painting steel constructions and large-capacity vehicles. Epoxy-resin-based coatings hardening at room temperature are suitable for a large variety of applications, e.g of. as high-grade acid- and solvent-resistant coatings whenever stoving is impracticable, e.g of. for pipelines, giant containers, boats, hulls, and heavy-duty corrosion prevention. Nitrocellulose lacquers are widely used in industrial furniture making, because they can be transparent or opacifying so that they are suitable both as primers and finishing lacquers. Nitrocellulose lacquers show the best pores pattern so that they are unique in accentuating the features of wood, especially in open-pore lacquer coats. Said coatings are completely resistant to moisture, sufficiently resistant to alcohol, but not resistant to organic solvents. Modified phenolic resins are usually employed as bonding agents for engraving- and offset printing inks. Solvent resistance and barrier properties of such lacquers can be improved by the addition of metal acrylates.

Die metal salts of unsaturated, short-chain carboxylic acids are also suitable for making polymer films and sheets (PP or PET) which can be used for instance for packing products by enveloping, sticking, or welding. Examples of these applications include protective films and sheets for cell-phone displays, foodstuffs, glass apparatuses exposed to high pressures, and laminated sheet glass which can be prevented from rupture by applying a safety film or sheet.

The addition of metal salts of unsaturated, short-chain carboxylic acids enhances the barrier properties, scratch resistance, adhesion, and mechanical ultimate tensile strength in the applications described hereinabove.

Metal salts of unsaturated, short-chain carboxylic acids may be used both in organic and inorganic coatings, e.g of. by vacuum metalizing.

Another example of such inorganic coatings is the application of a metal-oxide coat to metals or commodities with a metallic or ceramic (also glass) surface. For example, aluminium is usually protected by an artificial oxide coat (cf. anodizing). Diffusion barriers for foodstuffs, e.g of. in the form of an alumina layer between two acrylic acid polymer layers, are another application. Such coating is useful for minimizing the oxygen transfer between the enveloped product and the environment.

Alumina is employed in many of the abovementioned applications. It has, however, the disadvantage of being solid, insoluble, and less reactive and, normally, is insoluble in organic compounds so that special equipment or reactions are needed to achieve incorporation.

It is the object of the present invention to take advantage of metal salts of unsaturated carboxylic acids, which may be used in various ways in substances or in combination with other materials, alone or in mixtures, in liquid (dissolved) or solid form, with which they are miscible/compatible and polymerizable and into which they can be incorporated by means of their reactive groups, by combining the advantages of unsaturated, short-chain carboxylic acids with those of metal oxides and/or metal salts.

The combination of polymerizable organic groups with bound ionic metals yields very hard materials which offer a wide variety of uses. Moreover, the interactions between Lewis acids and -bases allow to further increase the strengths of new materials comprised of the aforementioned Lewis acids or, after hydrolysis, Brönsted acids and the corresponding basic components.

Die advantages of polymerized compounds are their improved environmental compatibility and reduced odor nuisance.

It has now surprisingly been found that organic metal salts with at least one unsaturated, short-chain carboxyl group (3 to 7 carbon atoms) are especially suitable for the following uses:

Such metal-organic compounds are exceptionally useful for surface coatings. Besides the surprisingly high hardness combined with good scrub and scratch resistance said coatings cured by UV radiation, electron beam, or conventional chemical radical starters show good UV resistance and good adhesion to metals, mineral substrates, glass, and various organic polymeric materials. These positive effects may also be produced by addition of only small amounts of the metal-organic compounds to organic coating materials (resins or monomers in general).

Still another application is the field of 'Improved Polymer Materials'. By addition of the compounds described hereinabove improved and/or faster curing of plastics or resins can be achieved. In addition, the viscosities of the materials can also be varied during curing.

Also when blended with other metal compounds, e.g of. metal alcoholates or metal salts, such as Ti, Zr, or Si, the resultant coatings display the excellent properties set forth hereinbelow.

Polymeric particles can be obtained by polymerization within a solution or emulsion. This can be achieved even in aqueous systems, e.g of. by UV-initiated suspension-, emulsion-, or solution polymerization.

The metal-organic compounds described herein may be employed for example in sol-gel reactions (cf. the following reaction scheme using Al-acrylate):

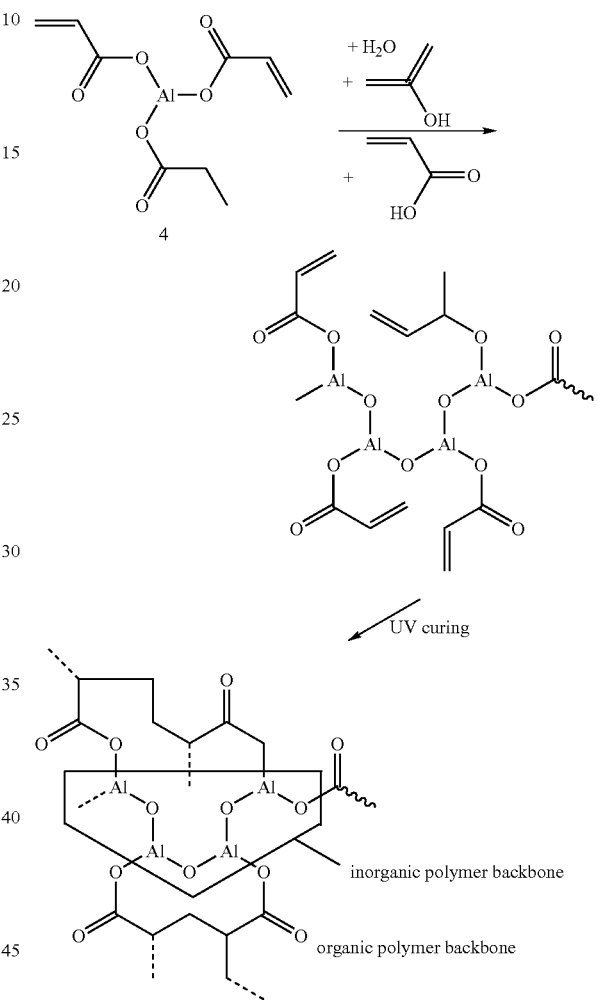

The metal-organic compounds described herein can be used advantageously in the following applications:
- monomer or co-monomer in polymerization processes, e.g of. for making, coating, or modifying moulded articles and/or films/sheets or for producing synthetic rubber
- additive in paints and lacquers
- carrier for pigments and dyes
- component in UV-curing adhesives or plastics
- for making comb polymers
- for producing or modifying organic and/or inorganic materials, such as ion-exchange resins, catalysts, and carriers (also for chromatographic applications)
- encapsulation of organic components by surface coating
- production of conductive materials, e.g of. for antistatic finish, in diaphragms, or for making PC boards
- additive for improving the resistance to chemicals and environmental effects, adhesion improver (e.g of. for mineral plasters), flow improver (e.g of. of concrete), and for sealing delicate objects scratch-resistant and/or hard coatings, e.g of. for metals, ceramics, wood or wood-based products, plastics, and glass for coating or treating leather, glass, paper, cardboard, plastics, metals, and textiles, hydrophilic or hydrophobic agents in the form of coatings or additives for making mould-release agents basic substance for producing antifouling paints for ships or maritime buildings protective coatings for forestry and agriculture, e.g of. as cut-end sealants for trees and in biocides electron-beam curing monomer in printing inks rheology modifier in barrier coatings against permeation of oxygen or water or microbial attack for making abrasives coating, adhesive, or therapeutic for pharmaceutics and/or in medical technology, e.g of. as dental cement, tooth enamel sealant, or delayed-action drug co-component for basic fillers, e.g of. glass, yielding exceptionally hard and resistant materials defoamer or defoaming products for producing and/or modifying inorganic products which may contain functional groups for producing and modifying ceramics.

EXAMPLES

Preparation of Liquid Metal Salts of Unsaturated Carboxylic Acids

The experiments were carried out in a 500-ml reaction flask made of glass and equipped with thermometer, stillhead, dropping funnel, stirrer, and gas supply. The first experiment was carried out under a nitrogen blanket, the second with compressed-air passage. The reaction heat was removed by water-bath cooling. The oxygen content in the gas used in the examples 2 to 7 was from 15 to 30 vol % (average 21 vol %). In the examples 8 to 10 the reaction mixture was saturated with oxygen.

Example 1

Preparation of Aluminium Tri-Acrylate in Solution (Comparative Example)

Into the flask described hereinabove there were placed 123.1 g of aluminium-tri-sec-butanolate, 119.9 g of diethylene glycol monobutyl ether, 0.7 g of 4-methoxyphenol, and 2 g of copper chips. To this mixture there were added in drops 108 grams of acrylic acid by means of a dropping funnel. The acid was added at room temperature (25° C.) during 1 hour and 4 minutes. Owing to the reaction heat, the temperature increased to 36° C. The mixture was cooled to 25° C. using a water bath and stirred for 23 minutes after which time the temperature increased again and the product gelled. Undesirably, the product polymerized, although polymerization inhibitors, such as copper chips and 4-methoxyphenol had been added during the reaction.

Example 2

Preparation of Aluminium Tri-Acrylate in Solution

Into the flask described hereinabove there were placed 102.1 g of aluminium triisopropanolate, 120.1 g of diethylene glycol monobutyl ether, and 0.7 g of 4-methoxyphenol. To this mixture there were added in drops using a dropping funnel 108 grams of acrylic acid. The acid was added during 15 minutes at room temperature (25° C.). Owing to the reaction heat, the temperature increased to 53° C. The mixture was cooled to 39° C. using a water bath. The product remained liquid and stable so that it could be further treated as follows, namely it was heated to 60° C. during 30 minutes and the co-product isopropanol was expelled during 2 hours using a continuous vacuum up to 243 mbar.

Example 3

Preparation of Aluminium Mono-acrylate-di-isopropanolate in Solution

Into the flask described hereinabove there were placed 142.9 g of aluminium tri-isopropanolate, 151.3 g of diethylene glycol monobutyl ether, and 0.7 g of 4-methoxyphenol. To this mixture there were added in drops using a dropping funnel 50.4 grams of acrylic acid. The acid was added during 8 minutes at room temperature (25° C.). Owing to the reaction heat, the temperature increased to 55° C. The product remained liquid and stable so that it could be heated to 60° C. during 30 minutes. The co-product isopropanol was expelled during 38 minutes using a continuous vacuum up to 245 mbar.

Example 4

Preparation of al-Mono-Acrylate-Di-Ethylacetoacetate in Solution

Into the flask described hereinabove there were placed 81.7 g of aluminium tri-isopropanolate and 0.7 g of 4-methoxyphenol. To this mixture there were added in drops using a dropping funnel 104.1 grams of ethyl acetoacetate. The acetate was added during 8 minutes at a temperature of 50° C. Owing to the reaction heat, the temperature increased to 61° C. After cooling to 32° C. by means of a water bath, 142.6 g of diethylene glycol monobutyl ether was added all at once and 28.8 g of acrylic acid then was quickly added in drops using a dropping funnel. The temperature thereby increased by 4° C. The product remained liquid and stable so that it could be heated to 60° C. during 30 minutes. The co-product isopropanol was expelled during 1 hour using vacuum up to 200 mbar.

Example 5

Preparation of Zirconium Tetra-acrylate in Solution

Into the flask described hereinabove there were placed 509.3 g of zirconium tetrabutanolate, 498.6 g of diethylene glycol monobutyl ether, and 2.8 g of 4-methoxyphenol. To this mixture there were quickly added in drops using a dropping funnel 382.7 grams of acrylic acid. The temperature thereby increased to 45° C. The product remained liquid and stable so that it could be heated to 90° C. during 30 minutes. The co-product butanol was expelled during 1 hour using vacuum up to 200 mbar.

Example 6

Preparation of Titanium Tetra-Acrylate in Solution (Not According to the Invention)

Into the flask described hereinabove there were placed 510.6 g of titanium-tetrabutanolate, 498.6 g of diethylene glycol monobutyl ether, and 2.8 g of 4-methoxyphenol. To this mixture there were quickly added in drops 432.6 grams of acrylic acid by means of a dropping funnel. The temperature thereby increased to 50° C. The product remained liquid and stable so that it could be heated to 90° C. during 30 minutes. The co-product butanol was expelled during 1 hour using vacuum up to 200 mbar.

Example 7

Preparation of Magnesium Di-Acrylate in Solution (Not According to the Invention)

Into the flask described hereinabove there were placed 510.55 g of magnesium dibutanolate, 498.6 g of diethylene glycol monobutyl ether, and 2.8 g of 4-methoxyphenol. To this mixture there were quickly added in drops 431.7 grams of acrylic acid by means of a dropping funnel. The temperature thereby increased to 48° C. The product remained liquid and stable so that it could be heated to 90° C. during 30 minutes. The co-product butanol was expelled during 1 hour using vacuum up to 200 mbar.

Preparation of Solid Metal Salts of Unsaturated Carboxylic Acids

Additional experiments were carried out for preparing solid metal compounds of unsaturated carboxylic acids.

General Prodecure/Equipment

The experiments were carried out in a 1,000-ml reaction flask made of glass and equipped with a rotary evaporator and vacuum pump. At a vacuum of 750 mbar the acrylic acid was sucked into the flask through a glass tube.

Example 8

Preparation of Solventless Aluminium Tri-Acrylate

Into the flask described hereinabove there were placed 204.2 grams of aluminium tri-isopropanolate to which 216 grams of acrylic acid were added during 8 minutes at room temperature (25° C.). The procedure was as set forth hereinabove. Owing to the reaction heat, the temperature increased to 32° C. The resultant product was a white, solid substance. The rotary evaporator heating then was switched on and gradually heated to 70° C. At the same time the vacuum was gradually adjusted to 24 mbar. The isopropanol was thereby expelled yielding a white powder.

Example 9

Preparation of Solventless Aluminium Monoacrylate Di-iso-propanolate

Into the flask described hereinabove there were placed 204.2 grams of aluminium tri-iso-propanolate to which 72 grams of acrylic acid were added during 8 minutes at room temperature (25° C.). The procedure was as set forth hereinabove. Owing to the reaction heat, the temperature increased to 32° C. The resultant product was a white, solid substance. The rotary evaporator heating then was switched on and gradually heated to 70° C. At the same time the vacuum was gradually adjusted to 24 mbar. The isopropanol was thereby expelled yielding a white powder.

Several experiments for producing this product in solution were carried out at the same conditions except that a 5.0-1 stainless-steel reactor was used in order to improve upscaling to commercial production. Owing to the use of pumps for supplying the acids, the feed time specified herein for the experiments in glass flasks was increased to 2 hours.

Example 10

Preparation of Solventless Zirconium Tetra-acrylate

Into the flask described hereinabove there were placed 1,021.3 g of zirconium tetrabutylate to which 767.5 grams of acrylic acid were added during 8 minutes at room temperature (25° C.). The procedure was as set forth hereinabove. Owing to the reaction heat, the temperature increased to 35° C. The resultant product was a white, solid substance. The rotary evaporator heating then was switched on and gradually heated to 90° C. At the same time the vacuum was gradually adjusted to 20 mbar. The butanol was thereby expelled yielding a white powder.

Contrary to the pungent odor of acrylic acid, the metal salts thereof prepared in the examples 2 to 10 are colourless and almost odorless.

Formulation 1

Formulation 1 is comprised of 50% aluminium tri-acrylate and 50% butyl triglycol. The resultant liquid was clear, slightly yellowish, viscous.

Formulation 2

Formulation 2 is comprised of 50% aluminium tri-methacrylate and 50% butyl triglycol. The resultant liquid was clear, slightly yellowish, viscous.

Formulation 3

Formulation 3 is comprised 31% aluminium tri-acrylate, 45% n-butylacrylate, and 24% 2-propanol. The resultant liquid was clear and slightly viscous.

Formulation 4

Formulation 4 is comprised of 30% aluminium tri-acrylate, 32% 2-hydroxyethyl-methacrylate, and 38% 2-butanol. The resultant liquid was clear and slightly viscous.

Formulation 5

Formulation 5 is comprised of 35% aluminium tri-methacrylate, 43% n-butyl-acrylate, and 22% 2-propanol. The resultant liquid was clear and slightly viscous.

Formulation 6

Formulation 6 is comprised of 21% aluminium tri-acrylate, 31% n-butylacrylate, and 48% hydroxyethylmethacrylate. The resultant liquid was clear and slightly viscous.

Formulation 7 (not According to the Invention)

Formulation 7 is comprised of 90% Formulation 3 and 10% tetra-n-butyl zirconate. The resultant liquid was clear and slightly viscous.

Formulation 8 (not According to the Invention)

Formulation 8 is comprised of 70% Formulation 3 and 30% tetra-n-butyl zirconate. The resultant liquid was clear and slightly viscous.

Formulation 9 (not According to the Invention)

Formulation 9 is comprised of 90% Formulation 3 and 10% tetra-n-butyl titanate. The resultant liquid was clear, slightly yellowish, slightly viscous.

Formulation 10 (not According to the Invention)

Formulation 10 is comprised of 70% Formulation 3 and 30% tetra-n-butyl titanate. The resultant liquid was clear, slightly yellowish, slightly viscous.

All of the formulations 1 to 10 also contain 3 wt. % photoinitiator (2,2-diethoxyacetophenone) and approx. 0.15-0.2 wt. % stabilizer (4-methoxy-phenol).

In the following exemplary applications (application 11 through 18) the reference substances for the formulations listed hereinabove were a commercially available white acrylic gloss paint of the DIY chain store Hornbach and a UV-curing adhesive gel (UV-1 phase gel of Wilke Cosmetics).

The acrylic paint was air-dried (no UV curing).

Application 11 Wolff-Wilborn Scratch Hardness (ISO 15184)

This test is done with pencils having different hardnesses, namely 6B to 9H. The pencils are drawn across a test specimen surface by means of a carriage fixed at an angle that allows to apply a constant force on different specimen supports. The film hardness is determined by the two marginal hardnesses between writing effect and indentation effect.

TABLE 1

|  | Glass | Poly-carbonate | Poly-propylene | Steel | Aluminium |
|---|---|---|---|---|---|
| Uncoated | >9H | 2B/B | B/HB | 8H/9H | 3B/2B |
| UV-cured adhesive gel | HB/F | <6B | <6B | 2B/B | 3B/2B |
| Acrylic paint (air drying) | F/H | F/H | 3B/2B | F/H | H/2H |
| Formulation 3 | H/2H | HB/F | 2B/B | 7H/8H | 6H/7H |
| Formulation 6 | F/H | HB/F | 4B/3B | — | H/2H |
| Formulation 7 | F/H | — | — | X | 2B/B |
| Formulation 8 | — | — | — | X | — |
| Formulation 9 | — | — | — | X | H/2H |
| Formulation 10 | — | — | — | X | — |

Legend:
X means that the test specimen did not have the corresponding coating.
— means that the film peeled off and the specimen could not be measured.
Pencil hardnesses from soft to hard: 6B, 5B, 4B, 3B, 2B, B, HB, F, H, 2H, 3H, 4H, 5H, 6H, 7H, 8H, 9H.

After UV curing followed by a seven-day storage period formulation 3 produced the best result on steel, glass, polypropylene, and aluminium. The scratch hardnesses of the formulation 3 coatings on polypropylene and aluminium were superior to those of uncoated materials. As to the polycarbonates, the acrylic-paint coating produced the best result.

Application 12 Clemen Scratch Hardness (ISO 1518)

This test is done by drawing a specimen at a defined force (0-20 N) under a hemispherically tipped hard-metal needle. The scratch hardness is defined as the force required for penetrating a coating by scratching. After UV curing followed by a seven-day storage period the following results were obtained:

TABLE 2

|  | Glass | Poly-carbonate | Poly-propylene | Steel | Aluminium |
|---|---|---|---|---|---|
| UV-cured adhesive gel | 10 | 5 | — | 15 | 13 |
| Acrylic paint (air drying) | 3 | 4 | 1 | 16 | 12 |
| Formulation 3 | 10 | 5 | 2 | 12 | 4 |
| Formulation 6 | 4 | 6 | 1 | — | 5 |
| Formulation 7 | 4 | — | — | X | 2 |
| Formulation 8 | — | — | — | X | — |
| Formulation 9 | — | — | — | X | 17 |
| Formulation 10 | — | — | — | X | — |

Legend:
X means that the test specimen did not have the corresponding coating.
— means that the film peeled off and the specimen could not be measured.

The acrylic-paint reference showed the best hardness on steel and a good result on aluminium. The best scratch hardness on aluminium was produced by formulation 9. The acrylic paint, formulation 3, formulation 6, and the UV-cured adhesive gel showed a poor scratch hardness on polycarbonate substrates. Formulation 3 and the UV-cured adhesive gel had the best scratch hardness on glass. The acrylic paint, formulation 3, and formulation 6 showed a poor scratch hardness on polypropylene specimens.

Application 13 König Pendulum Hardness (DIN 53157, ISO 1522)

In this test the damping of a pendulum swinging on a coating is evaluated at defined conditions. The pendulum is mounted on two steel hemispheres, which are set swinging on the coating under examination. A high swing number means high

TABLE 3

|  | Glass | Poly-carbonate | Poly-propylene | Steel | Aluminium |
|---|---|---|---|---|---|
| UV-cured adhesive gel | 48 | 56 | 25 | 42 | 32 |
| Acrylic paint (air drying) | 141 | 196 | 113 | 83 | 132 |
| Formulation 3 | 180 | 202 | — | 162 | 206 |
| Formulation 6 | 160 | 191 | 115 | — | 189 |
| Formulation 7 | 119 | — | — | X | 179 |
| Formulation 8 | — | — | — | X | — |
| Formulation 9 | — | — | — | X | 193 |
| Formulation 10 | — | — | — | X | 182 |

Legend:
X means that the test specimen did not have the corresponding coating.
— means that the film peeled off and the specimen could not be measured.

Formulation 3 showed the best pendulum hardness on glass, polycarbonate, steel, and aluminium. As to polypropylene, formulation 6 and the acrylic paint produced good results, whereas formulation 3 peeled off.

Application 14 Time Factor

The advantages of the abovementioned formulations are yet more distinct when considering the time.

For example, the formulations under examination proved to be good both after a short time (formulation 3) and after several days of storage (formulation 6), which makes them suitable for various applications.

TABLE 4

| Clemen Scratch Hardness | Glass | | | Polycarbonate | | | Polypropylene | | | Steel | | | Aluminium | | |
|---|---|---|---|---|---|---|---|---|---|---|---|---|---|---|---|
| | | | | | | Storage time after UV curing | | | | | | | | | |
| (ISO 1518) | 1 h | 1 D | 7 D | 1 h | 1 D | 7 D | 1 h | 1 D | 7 D | 1 h | 1 D | 7 D | 1 h | 1 D | 7 D |
| UV-cured adhesive gel | 12 | 9 | 10 | 5 | 11 | 5 | 3 | 3 | — | 19 | 16 | 15 | 11 | 11 | 13 |
| Acrylic paint (air drying) | 5 | 4 | 3 | 4 | 4 | 4 | 1 | 1 | 1 | 10 | 10 | 16 | 6 | 7 | 12 |
| Formulation 1 | 4 | 6 | 12 | 5 | 4 | — | <1 | — | — | 4 | 4 | — | 5 | 4 | — |
| Formulation 3 | 4 | 8 | 10 | 2 | 7 | 5 | 2 | 2 | 2 | 3 | 7 | 10 | 5 | 6 | 4 |

TABLE 4-continued

| Clemen Scratch Hardness | Glass | | | Polycarbonate | | | Polypropylene | | | Steel | | | Aluminium | | |
|---|---|---|---|---|---|---|---|---|---|---|---|---|---|---|---|
| | | | | | | Storage time after UV curing | | | | | | | | | |
| (ISO 1518) | 1 h | 1 D | 7 D | 1 h | 1 D | 7 D | 1 h | 1 D | 7 D | 1 h | 1 D | 7 D | 1 h | 1 D | 7 D |
| Formulation 6 | 1 | 6 | 4 | 2 | 5 | 6 | 1 | 1 | 1 | 1 | 4 | — | 1 | 5 | 5 |
| Formulation 7 | 2 | 2 | 5 | 3 | 2 | — | 3 | 2 | — | X | X | X | 2 | 2 | 2 |
| Formulation 8 | — | — | — | — | — | — | — | — | — | X | X | X | — | — | — |
| Formulation 9 | 5 | 2 | — | — | — | — | — | — | — | X | X | X | 10 | 13 | 17 |
| Formulation 10 | 5 | 7 | — | — | — | — | — | — | — | X | X | X | 2 | 4 | — |

TABLE 5

| König Pendulum Hardness (DIN 53157/ | Glass | | | Polycarbonate | | | Polypropylene | | | Steel | | | Aluminium | | |
|---|---|---|---|---|---|---|---|---|---|---|---|---|---|---|---|
| | | | | | | Storage time after UV curing | | | | | | | | | |
| ISO 1522) | 1 h | 1 D | 7 D | 1 h | 1 D | 7 D | 1 h | 1 D | 7 D | 1 h | 1 D | 7 D | 1 h | 1 D | 7 D |
| UV-cured adhesive gel | 55 | 48 | 48 | 42 | 91 | 56 | 25 | 45 | 25 | 22 | 56 | 42 | 20 | 50 | 32 |
| Acrylic paint (air drying) | 83 | 127 | 141 | 167 | 183 | 196 | 85 | 118 | 113 | 34 | 69 | 83 | 74 | 134 | 132 |
| Formulation 1 | 137 | 174 | — | 200 | 199 | 182 | 105 | — | — | 129 | 158 | 123 | 118 | 181 | 133 |
| Formulation 3 | 147 | 179 | 180 | 207 | 220 | 202 | 127 | 111 | — | 136 | 160 | 162 | 185 | 188 | 206 |
| Formulation 6 | 24 | 118 | 160 | 35 | 144 | 164 | 49 | 90 | 115 | 27 | 111 | — | 27 | 120 | 189 |
| Formulation 7 | 105 | 136 | 119 | 69 | 81 | — | 89 | 92 | — | X | X | X | 115 | 153 | 179 |
| Formulation 8 | — | — | — | — | — | — | — | — | — | X | X | X | — | — | — |
| Formulation 9 | 121 | 179 | — | — | — | — | — | — | — | X | X | X | 176 | 176 | 193 |
| Formulation 10 | 183 | 189 | — | — | — | — | — | — | — | X | X | X | 186 | 190 | 182 |

TABLE 6

| Wolff-Wilborn Scratch Hardness | Glass | | | Polycarbonate | | | Polypropylene | | |
|---|---|---|---|---|---|---|---|---|---|
| | | | | Storage time after UV curing | | | | | |
| (ISO 15184) | 1 h | 1 D | 7 D | 1 h | 1 D | 7 D | 1 h | 1 D | 7 D |
| UV-cured adhesive gel | 3B/2B | B/HB | HB/F | 4B/3B | 3B/2B | >6B | 6B/5B | >6B | >6B |
| Acrylic paint (air drying) | B/HB | HB/F | F/H | HB/F | F/H | F/H | 3B/2B | 3B/2B | 3B/2B |
| Formulation 3 | B/HB | HB/F | H/2H | F/H | B/HB | HB/F | 2B/B | 2B/B | 2B/B |
| Formulation 6 | <6B | B/HB | F/H | 6B/5B | B/HB | HB/F | <6B | 5B/4B | 4B/3B |
| Formulation 7 | F/H | F/H | F/H | 5B/4B | 5B/4B | — | 4B/3B | 4B/3B | — |
| Formulation 8 | — | — | — | — | — | — | — | — | — |
| Formulation 9 | F/H | F/H | — | — | — | — | — | — | — |
| Formulation 10 | — | — | — | — | — | — | — | — | — |

| Wolff-Wilborn Scratch Hardness | Steel | | | Aluminium | | |
|---|---|---|---|---|---|---|
| | | | Storage time after UV curing | | | |
| (ISO 15184) | 1 h | 1 D | 7 D | 1 h | 1 D | 7 D |
| UV-cured adhesive gel | 3B/2B | HB/F | 2B/B | 2B/B | 3B/2B | 3B/2B |
| Acrylic paint (air drying) | 3B/2B | HB/F | F/H | B/HB | HB/F | H/2H |
| Formulation 3 | F/H | H/2H | 7H/8H | F/H | H/2H | 6H/7H |
| Formulation 6 | 6B/5B | B/HB | — | 6B/5B | H/2H | H/2H |
| Formulation 7 | X | X | X | 2H/3H | 2H/3H | 2B/B |
| Formulation 8 | X | X | X | — | — | — |
| Formulation 9 | X | X | X | 6B/5B | 6B/5B | H/2H |
| Formulation 10 | X | X | X | HB/F | F/H | H/2H |

Legend:
X means that the test specimen did not have the corresponding coating.
— means that the film peeled off and the specimen could not be measured.
Pencil hardnesses from soft to hard: 6B, 5B, 4B, 3B, 2B, B, HB, F, H, 2H, 3H, 4H, 5H, 6H, 7H, 8H, 9H.

Application 15 Tesa® Abriss (Adhesion Test)

A Tesa® strip was applied to a coating and then pulled off abruptly and vigorously. The coating condition was rated from 0 to 4 (cf. table below).

TABLE 7

| | Rating | | | | |
|---|---|---|---|---|---|
| | 0 | 1 | 2 | 3 | 4 |
| Pull-off, in % | 0 (none) | <25 | 50 | >50 | 100 (complete pull-off of the coating area under the adhesive strip) |

The acrylic paint, formulation 3, and formulation 6 showed 100% adhesion to glass, steel, and aluminium. Only the UV-cured adhesive gel adhered to the polycarbonate surface. When applied to polypropylene, all of the described coatings peeled off at 100%.

TABLE 8

| | Glass | Poly-carbonate | Poly-propylene | Steel | Aluminium |
|---|---|---|---|---|---|
| UV-cured adhesive gel | 0 | 0 | 4 | 0 | 4 |
| Acrylic paint (air drying) | 0 | 4 | 4 | 0 | 0 |
| Formulation 3 | 0 | 4 | 4 | 0 | 0 |
| Formulation 6 | 0 | 4 | — | 0 | 0 |
| Formulation 7 | 0 | — | — | X | 2 |
| Formulation 8 | — | — | — | X | — |
| Formulation 9 | — | — | — | X | 0 |
| Formulation 10 | — | — | — | X | 0 |

Legend:
X means that the test specimen did not have the corresponding coating.
— means that the film peeled off and the specimen could not be measured.

Application 16 Cross-Cut Test

This test is carried out for evaluating the elasticity of coatings. A right-angle lattice pattern is sharply cut into the coating using a standard steel lamella. The rating is similar to the peeling test except that the percentage graduation is different.

TABLE 9

| | Rating | | | | |
|---|---|---|---|---|---|
| | 0 | 1 | 2 | 3 | 4 |
| Peeled cut edges, in % | clean edges | 5 | 15 | 35 | 65 |

The cross-cut test was carried out on UV-cured coatings which had been stored for seven days in a conditioning room. The UV-cured adhesive gel and the acrylic paint produced the best results on glass, whereas on polycarbonate the acrylic paint, the UV-cured adhesive gel, and the formulations 3 and 6 turned out to be the best. Only the acrylic paint performed well on polypropylene. Formulation 3 and the UV-cured adhesive gel produced very good results on steel, whereas the acrylic paint was significantly inferior. Excellent film properties were found with each of the formulations and reference substances tested when applied to aluminium.

TABLE 10

| | Glass | Poly-carbonate | Poly-propylene | Steel | Aluminium |
|---|---|---|---|---|---|
| UV-cured adhesive gel | 0 | 0 | 4 | 0 | 0 |
| Acrylic paint (air drying) | 0 | 0 | 0 | 4 | 0 |
| Formulation 3 | 1 | 0 | — | 0 | 0 |
| Formulation 6 | 1 | 0 | — | — | 0 |
| Formulation 7 | 2 | — | — | X | 0 |
| Formulation 9 | — | — | — | X | 0 |
| Formulation 10 | — | — | — | X | 0 |

Legend:
X means that the test specimen did not have the corresponding coating.
— means that the film peeled off and the specimen could not be measured.

Application 17 Scrub Resistance

This test was done using a commercially available scrubbing sponge fixed in a carriage moved across the coating under examination. The to-and-fro motion of the machine-moved carriage was measured in cycles (once to and fro was one cycle). The result was expressed by the number of cycles the coating withstood without destruction. The test was discontinued after max. 5,000 cycles. Sponge and carriage weighed 134 grams, i.e. a pressure of 4 $g/cm^2$. The film thickness of the tested formulations and reference substances was 50 µm wet. The storage after UV curing corresponded to the conditions specified in the relevant standard.

Formulation 3 and the UV-cured adhesive gel had a scrub resistance of >5,000 cycles for any of the possible storage times. The films showed scrub traces but were still intact. The scrub resistance of formulation 6 improved with longer storage times, whereas the acrylic paint fell off.

TABLE 11

| | Cycles after 1-hour storage time | Cycles after 24-hour storage time | Cycles after 7-day storage time |
|---|---|---|---|
| Acrylic paint (air drying) | 2,400 | 3,200 | 1,500 |
| UV-cured adhesive gel | >5,000 | >5,000 | >5,000 |
| Formulation 3 | >5,000 | >5,000 | >5,000 |
| Formulation 6 | 840 | 1,200 | 4,500 |

Application 18 Pull-Off Adhesion Test (following ASTM D 4541)

TABLE 12

| | UV-Cured Adhesive Gel Storage time after UV curing | | Formulation 3 | | Acrylic Paint Air drying |
|---|---|---|---|---|---|
| Test Specimen | 1 day | 7 days | 1 day | 7 days | 14 days |
| Glass | 2.0 | >3.5 | 3.5 | 2.5 | 1.0 |
| Polypropylene | <0.5 | <0.5 | <0.5 | <0.5 | X |
| Polycarbonate | 0.5 | <0.5 | 0.5 | 1.0 | X |
| PVC | <0.5 | 0.5 | <0.5 | 0.5 | X |
| Steel | 1.0 | 1.0 | 1.25 | 1.25 | X |
| Aluminium | 0.5 | 0.5 | 0.5 | 0.5 | 1.0 |
| Copper | 0.5 | 0.5 | 1.0 | 1.0 | X |

Legend:
X means that the test specimen did not have the corresponding coating.

The pull-off adhesion test was carried out as follows. The coating was stored for some time in a conditioning room. Several carefully degreased or sanded test dollies were glued to the coating by means of a 2-component epoxy adhesive.

Excess adhesive was removed. The hardening time was 8 hours at 23° C. The tensile stress on the test dolly was gradually increased until the dolly was pulled off. The result was recorded as the tensile stress measured in N/mm at the instant of pull-off. According to ASTM D 4541, at least three individual tests are required for a reliable statement.

Among the coatings tested, namely acrylic paint, UV-cured adhesive gel, and formulation 3, the coatings containing the latter one showed the poorest adhesion to steel, copper, and polycarbonate, i.e. they failed the test already after 1-day storage after UV curing. The coatings containing either UV-cured adhesive gel or formulation 3 gave the same results when glued to polypropylene and PVC. When glued to glass, the UV-cured adhesive gel was superior after a seven-day storage time, whereas formulation 3 fell off.

Application 19 Rheology

Printing-ink resins require a precise rheology in order to allow high-speed printing. The apparent viscosity is essential for determining the Theological data. The effect on the apparent viscosity of printing-ink resins by addition of various formulations containing metal acrylates was examined. The reference materials of choice were an untreated printing-ink resin and a resin containing DOROX® D 515.

None of the specimens under examination failed the rheological tests.

TABLE 13

| Specimen | Test Temperature [° C.] | Al Content in Resin [%] | Apparent Viscosity at 50 s$^{-1}$ [Pa · s] | Apparent Viscosity at 5 s$^{-1}$ [Pa · s] |
|---|---|---|---|---|
| Printing-ink resin (PIR) | 20 | 0.000 | 134 | 152 |
| PIR + DOROX ® D 515 | 20 | 0.060 | 204 | 292 |
| PIR + DOROX ® D 515 | 20 | 0.080 | 226 | 362 |
| PIR + DOROX ® D 515 | 20 | 0.100 | 269 | 491 |
| PIR + Formulation 1 | 20 | 0.060 | 203 | 297 |
| PIR + Formulation 1 | 20 | 0.080 | 284 | 495 |
| PIR + Formulation 1 | 20 | 0.100 | 246 | 459 |
| PIR + Formulation 2 | 20 | 0.060 | 205 | 295 |
| PIR + Formulation 2 | 20 | 0.080 | 248 | 395 |
| PIR + Formulation 2 | 20 | 0.100 | 278 | 473 |

Application 20 Water Absorption of Paper

Standard-quality papers coated on both sides with the formulations 1, 3 or 6 in a film thickness of 50 μm were used for this test. The reference material of choice was untreated paper. The papers were exposed to UV light and were immersed in water one hour later for 2 or 24 hours. In another test the papers were again immersed in water for 2 hours or 24 hours seven days after exposure to UV light. The water absorption was measured in percent by weighing the papers and recording the weight difference.

The paper coated with formulation 3 had the lowest water absorption in the examination after one-hour storage after UV exposure. After a 7-day storage time the papers coated with formulation 6 had the lowest water absorption.

TABLE 14

| | Water Absorption in % after Immersion in Water | | | | | | | |
|---|---|---|---|---|---|---|---|---|
| | 2 h | 2 h | 24 h | 24 h | 2 h | 2 h | 24 h | 24 h |
| Untreated Paper | 101.4 | 101.1 | 105.0 | 104.6 | — | — | — | — |
| | 1 h after UV exposure | | | | 7 days after UV exposure | | | |
| Formulation 1 | 38.4 | 38.3 | 41.7 | 49.1 | 65.6 | 74.6 | 72.3 | 82.7 |
| Formulation 3 | 37.2 | 37.0 | 37.6 | 36.6 | 56.0 | 56.0 | 57.8 | 57.9 |
| Formulation 6 | 40.7 | 39.7 | 44.2 | 43.5 | 33.6 | 30.2 | 41.5 | 39.4 |

Application 21 UV Exposure of Aluminium-Acrylate Formulations on Glass

The formulations 3, 6 and 1 were applied in a wet-film thickness of 50 μm to a glass substrate and subjected to UV curing. These specimens then were exposed to UV light during 225 hours at approx. 54° C. The evaluation was made following DIN 55980 ('blue-yellow value'). According to said German standard, a positive blue-yellow value means a tinge of yellow, whereas a negative value means a tinge of blue. The blank value of the calibration tile was +7.24.

TABLE 15

| Specimen | Initial Value | Value after UV Exposure |
|---|---|---|
| Formulation 3 | +7.51 | +7.40 |
| Formulation 6 | +7.44 | +7.54 |
| Formulation 1 | +7.62 | +6.97 |

The 'blue-yellow values' of UV-exposed films were below or slightly different from the initial value, i.e. the coatings are not susceptible to yellowing.

Application 22 Chemicals Resistance

The formulations 3, 6 and 1 and the UV-cured adhesive gel were applied in a film thickness of 50 μm to glass and subjected to UV curing. After a storage time of 1 hour and 24 hours the films were exposed during 2 hours to the following chemicals: methyl ethyl ketone, 2-propanol, acetic acid, phosphoric acid, mineral oil, and 30% sodium hydroxide solution.

TABLE 16

| | MEK | | 2-Propanol | | Acetic Acid | | Phosphoric Acid | | Mineral Oil | | 30% Sodium Hydroxide | |
|---|---|---|---|---|---|---|---|---|---|---|---|---|
| | Storage Time after UV Curing | | | | | | | | | | | |
| | 1 h | 24 h | 1 h | 24 h | 1 h | 24 h | 1 h | 24 h | 1 h | 24 h | 1 h | 24 h |
| UV-cured adhesive gel | − | + | − | + | − | − | − | − | + | + | +/− | +/− |
| Formulation 1 | +/− | a | + | a | − | − | − | − | +/− | a | − | − |
| Formulation 2 | − | − | +/− | − | − | − | − | − | +/− | + | − | − |

TABLE 16-continued

|  | MEK | | 2-Propanol | | Acetic Acid | | Phosphoric Acid | | Mineral Oil | | 30% Sodium Hydroxide | |
|---|---|---|---|---|---|---|---|---|---|---|---|---|
|  | \multicolumn{12}{c}{Storage Time after UV Curing} |
|  | 1 h | 24 h | 1 h | 24 h | 1 h | 24 h | 1 h | 24 h | 1 h | 24 h | 1 h | 24 h |
| Formulation 3 | +/− | + | + | + | − | − | − | − | + | + | − | − |
| Formulation 6 | − | +/− | − | + | − | − | − | − | − | + | − | − |

Legend:
− unresistant
+/− film shows traces of attack but is yet intact
+ resistant
a peeled off After UV curing and storage for just one hour the films of formulation 3 were completely or partially resistant to methyl ethyl ketone, 2-propanol, and mineral oil. The UV-cured adhesive gel and formulation 6 required a storage time of 24 h to become resistant to said chemicals except that the UV-cured adhesive gel was resistant to mineral oil after one hour already. The UV-cured adhesive gel turned out to be partially resistant to 30% sodium hydroxide solution. None of the substances tested was resistant to acids.

Application 23 Functional Sportswear Coating

Functional sportswear fabric was made water-repellent by coating with formulation 3 and exposure to UV light. The water sprayed onto the fabric formed drops on its surface. No water was absorbed, whereas untreated fabric absorbed the water immediately. The fabric then was washed with soap-suds, dried, and exposed again to water spraying after a storage time of 3 weeks. The same positive result was obtained.

The invention claimed is:

1. A method for preparing metal salts of unsaturated, short-chain carboxylic acids by reacting in a solution
    a metal-alcoholate compound and
    a compound selected from the group consisting of carboxylic acids of the general formula:

$C_nH_{2n-1}C(=O)OH$, wherein the double bond is in the 2- or 3-position and
    n represents 2, 3, 4, 5, or 6, maleic acid and mixtures thereof, in the presence of oxygen ($O_2$), which is continuously fed so that the reaction solution is at least 50% oxygen-saturated, to produce metal salts having at least one group of the formula $C_nH_{2n-1}C(=O)O^-$ and/or $-OC(=O)CH=CHC(=O)O-(H^+)$ and a metal (M) selected from the group consisting of Al, Si, Sn, La, Zr, Cu and Zn and mixtures thereof.

2. The method of claim 1, characterized in that oxygen is continuously fed so that the reaction solution is at least 90% oxygen-saturated.

3. The method of claim 1, characterized in that the metal salts have the general formula $M(OOCC_nH_{2n-1})_a(R^1)_b$ and can be obtained by reaction of a linear or branched, unsaturated carboxylic acid of the formula $C_nH_{2n}-COOH$, wherein n represents 2, 3, 4, 5, or 6 with the double bond in 2- or 3-position, with a metal compound of the general formula $M(R^1)_c$ and, optionally, $H(R^1)$, wherein
    a is at least 1,
    b is 0, 1, 2 or 3 and
    (a+b) and c are independently of one another an integer of 2 to 4,
    $R^1$ represents an alcoholate group having a $C_1$- to $C_6$ hydrocarbon residue, wherein $R^1$ is an alcoholate group, which can be obtained from an alcohol having at least one —OH group, or $$R^2-\overset{O-}{C}=CH-C(=O)O-R^3,$$

wherein $R^2$ and respectively $R^3$ represent —$CH_3$, —$C_2H_5$, —$C_3H_7$ or —$C_4H_9$ and n, $R^1$, $R^2$, and $R^3$ may be different for each a, b, and c and at least one $R^1$ in $M(R^1)_c$ represents an alcoholate group having a $C_1$- to $C_6$ hydrocarbon residue.

4. A method according to claim 1, characterized in that the reaction is carried out in the presence of continuously fed oxygen in a gas mixture containing the oxygen in a concentration from 5 to 30, preferably 15 to 25 vol %.

5. A method according to claim 1, characterized in that the reaction is carried out at temperatures from 0 to 150° C.

6. A method according to claim 1, characterized in that the reaction is carried out at pressures from $bar_{abs}$ to 0.01 $bar_{abs}$.

7. A method according to claim 1, characterized in that the reaction is carried out without a solvent.

8. A method according to claim 1, characterized in that the reaction is carried out in at least one of the following solvents: hydrocarbons, esters, ethers, glycols, and glycol mono- or diethers.

9. A method according to claim 1, characterized in that the carboxylic acid is acrylic acid or methacrylic acid.

10. A method according to claim 1, characterized in that the metal M is aluminium and/or zirconium.

11. A method according to claim 1, characterized in that the metal compound is a metal alcoholate.

12. A method according to claim 1, characterized in that the reaction is carried out in the substantial absence of water.

13. A method according to claim 5, characterized in that the reaction is carried out at temperatures from 20 to 100° C.

* * * * *

UNITED STATES PATENT AND TRADEMARK OFFICE
CERTIFICATE OF CORRECTION

| | |
|---|---|
| PATENT NO. | : 7,943,798 B2 |
| APPLICATION NO. | : 10/563237 |
| DATED | : January 25, 2011 |
| INVENTOR(S) | : Peter Finmans |

It is certified that error appears in the above-identified patent and that said Letters Patent is hereby corrected as shown below:

Column 19, line 43, "(0" should read --(O--.

Column 19, line 61, "2n-" should read --2n-1--.

Column 20, line 30, "O—" should read "O-"

Column 20, line 46, please insert the number --2-- between "from" and "bar".

Signed and Sealed this
Second Day of August, 2011

David J. Kappos
*Director of the United States Patent and Trademark Office*